United States Patent [19]
Mehlhorn

[11] Patent Number: 5,622,713
[45] Date of Patent: Apr. 22, 1997

[54] METHOD OF DETOXIFYING ANIMAL SUFFERING FROM OVERDOSE

[75] Inventor: Rolf J. Mehlhorn, Richmond, Calif.

[73] Assignee: The Regents of the University of California, Alameda, Calif.

[21] Appl. No.: 375,190

[22] Filed: Jan. 18, 1995

Related U.S. Application Data

[63] Continuation of Ser. No. 992,586, Dec. 18, 1992, abandoned, which is a continuation of Ser. No. 547,382, Jul. 3, 1990, abandoned, which is a continuation of Ser. No. 220,388, Jul. 12, 1988, abandoned, which is a continuation of Ser. No. 776,826, Sep. 17, 1985, abandoned.

[51] Int. Cl.$^6$ ..................................................... A61K 9/127
[52] U.S. Cl. .................... 424/450; 264/4.3; 428/402.2; 514/812; 514/823
[58] Field of Search .................... 264/4.3; 428/402.2; 424/10, 450; 436/829; 514/823, 812

[56] References Cited

U.S. PATENT DOCUMENTS

| | | | |
|---|---|---|---|
| 3,522,346 | 7/1970 | Chang | 424/10 X |
| 3,804,776 | 4/1974 | Yazawa et al. | |
| 4,053,585 | 10/1977 | Allison et al. | |
| 4,241,046 | 12/1980 | Papahadjopoulos et al. | |
| 4,244,816 | 1/1981 | Vogler et al. | |
| 4,310,505 | 1/1982 | Baldeschwieler et al. | |
| 4,397,846 | 8/1983 | Weiner et al. | |
| 4,411,894 | 10/1983 | Schrank et al. | |
| 4,427,649 | 1/1984 | Dingle et al. | |
| 4,946,683 | 8/1990 | Forssen | |
| 5,192,549 | 3/1993 | Barenolz et al. | 424/450 |
| 5,204,112 | 4/1993 | Hope et al. | 424/450 |

FOREIGN PATENT DOCUMENTS

| | | |
|---|---|---|
| 0088046 | 9/1983 | European Pat. Off. |
| WO8601102 | 2/1986 | WIPO |

OTHER PUBLICATIONS

Bally, M. B., et al., "Uptake of Safranine and Other Lipophilic Cations into Model Membrane Systems in Response to a Membrane Potential", *Biochim. Biophys. Acta*, 812:66–76 (1985).

Mayer, L. D., et al., "Uptake of Antineoplastic Agents into Large Unilameller Vesicles in Response to a Membrane Potential", *Biochim. Biophys. Acta*, 816:294–302 (1985).

Rottenberg, H., "The Measurement of Membrane Potential and Δ pH in Cells, Organelles, and Vesicles", *Meth. Enzymol.*, 55:547–569 (1979).

Reinhold, L., et al., "Membrane Transport of Sugars and Amino Acids", *Ann. Rev. Plant Physiol.*, 35:45–83 (1984).

Mehlhorn, R., et al., "Light–Induced pH Gradients Measured with Spin–Labelled Amine and Carboxylic Acid Probes:Application to *Halobacterium Halobium* Cell Envelope Vesicles", *Meth. Enzymol.*, 88:334–344 (1982).

Melandri, B., et al., "Light–Induced Proton Gradients and Internal Volumes in Chromatophores of *Rhodopseudomonas Spheaeroids*", *Arch. Biochem. Biophys.*, 235:97–105 (1984).

Miyamoto, V. K., et al., "Preparation and Characteristics of Lipid Vesicles", *J. Membrane Biol.*, 4:252–269 (1971).

Cafiso, D. S., et al., "Electrogenic $H^+/OH^-$ Movement Across Phospholipid Vesicles Measured by Spin–Labeled Hydrophobic Ions", *Biophys. J.*, 44:49–57 (1983).

Casey, R. P., et al., "Active Proton Uptake by Chromaffin Granules:Observation by Amine Distribution and Phosphorus–31 Nuclear Magnetic Resonance Techniques", *Biochemistry*, 16:972–976 (1977).

Cramer, J. A., et al., "NMR Studies of pH–Induced Transport of Carboxylic Acids Across Phospholipid Vesicle Membranes", *Biochem. Biophys. Res. Commun.*, 75(2):295–301 (1977).

Kirby, C., et al., "This Effect of Lipid Composition of Small Unilamellar Liposomes containing Melphalan and Vincristine on Drug Clearance after Injection into Mice", *Biochem. Pharmac.*, 32(4):609–615 (1983).

Kornberg, R. D., et al., "Measurement of Transmembrane Potentials in Phospholipid Vesicles", *Proc. Nat. Acad. Sci.*, 69(6):1508–1513 (1972).

Nichols, J. W., et al., "Catecholamine Uptake and Concentration by Liposomes Maintaining pH Gradients", *Biochem. Biophys. Acta*, 455:269–271 (1976).

Deamer, D. W., et al., "The Response of Fluorescent Amines to pH Gradients Across Liposomes Membranes", *Biochem. Biophys. Acta*, 274:323–335 (1972).

Garcia, M. L., et al., "Mechanism of Lactose Translocation in Proteo Liposomes Reconstituted with lac Carrier Protein Purified from *Escherichia coli*. 1. Effect of pH and Imposed Membrane Potential on Efflux, Exchange and Counterflow", *Biochemistry*, 22:2524–2531 (1983).

(List continued on next page.)

*Primary Examiner*—Richard D. Lovering
*Attorney, Agent, or Firm*—Burns, Doane, Swecker & Mathis, L.L.P.

[57] ABSTRACT

A method for accumulating drugs or other chemicals within synthetic, lipid-like vesicles by means of a pH gradient imposed on the vesicles just prior to use is described. The method is suited for accumulating molecules with basic or acid moieties which are permeable to the vesicles membranes in their uncharged form and for molecules that contain charge moieties that are hydrophobic ions and can therefore cross the vesicle membranes in their charged form.

The method is advantageous over prior art methods for encapsulating biologically active materials within vesicles in that it achieves very high degrees of loading with simple procedures that are economical and require little technical expertise, furthermore kits which can be stored for prolonged periods prior to use without impairment of the capacity to achieve drug accumulation are described.

A related application of the method consists of using this technology to detoxify animals that have been exposed to poisons with basic, weak acid or hydrophobic charge groups within their molecular structure.

2 Claims, 2 Drawing Sheets

OTHER PUBLICATIONS

Kano, K., et al., "Pyranine as a Sensitive pH Probe for Liposome Interiors and Surfaces. pH Gradients Across Phospholipid Vesicles", *Biochem. Biophys. Acta,* 509:289–299 (1978).

Shakov, Y. A., et al., "Reconstitution of Highly Purified Proton–translocating Pyrophosphatase from *Rhodospirillum Rubrum*", *Biokhimiya,* 48(8):1347–1351 (1983).

Shinbo, T., et al., "Photoredox Reaction in Membrane Potential in the Liposome System", *J. Chem. Soc. Japan,* 6:917–923 (1983).

Corda, D., et al., "Increase in Lipid Microviscosity of Uniamellar Vesicles upon the Creation of Transmembrane Potential", *J. Membrane Biol.,* 65:235–242 (1982).

Ivkov, F. G., et al., "Redistribution of Positively Charged Probes in Membrane Suspension under the Action of Transmembrane Potential", *Gen. Physiol. Biophys.,* 3:19–30 (1984).

5,622,713

METHOD OF DETOXIFYING ANIMAL SUFFERING FROM OVERDOSE

Acknowledgement of Government Support

This invention was made with Government support under Grant No: DE-AC03-76SF00098 with the Department of and the University of California. The Government has the rights in this invention.

This application is a continuation of application Ser. No. 07/992,586, Dec. 18, 1992 and now abandoned; which is a continuation of Ser. No. 07/547,382, filed Jul. 3, 1990 and now abandoned; which is a continuation of Ser. No. 07/220,388, filed Jul. 12, 1988 and now abandoned; which is a continuation of application Ser. 06/776,826, filed Sep. 17, 1985 and now abandoned.

TECHNICAL FIELD

The invention relates to a method for loading lipid-like vesicles with a drug or other chemical species by establishing a preimposed pH gradient.

BACKGROUND ART

The use of membranous vesicles such as liposomes and the like as adjuvants and carriers for drugs, other chemicals and biologically active compounds such as antigens and antibodies is well known in the field (U.S. Pat. Nos. 4,053, 585; 4,397,846; 4,411,894; 4,427,649).

Also, many methods exist to encapsulate the various drugs or other chemicals within the vesicles. U.S. Pat. No. 4,241,046, discloses a method for encapsulating biologically active materials within liposomes by providing a combination of lipids in an organic solvent and an aqueous mixture of the material for encapsulation, emulsifying the provided mixture, removing the organic solvent, and suspending the resulting gel in water. The biologically active material is encapsulated by being processed with the liposome during preparation of the liposome.

U.S. Pat. No. 3,804,776 discloses a method for producing oil and fat encapsulated amino acids or polypeptides by dispersion. Powders of the material desired to be encapsulated are combined in a molten mixture of the lipid material. Thereafter the molten mixture is poured into water. This method of encapsulation, however, only allows for oral administration of the encapsulated material, since the droplets of lipids enclosing the encapsulted material are too large to be delivered parenterally.

Most of the other known methods also involve encapsulating the desired drug or other chemical during the synthesis of the liposome (Papahadjopoulos, et al., *Biochim., Biophys. Acta*, 135:639 (1967); Bangham et al., *J. Mol. Biol.*, 12:238–252 (1965); and Bapzri and Korn, *Biochim., Biophys. Acta*, 298:1015 (1973)). All of the methods described, either employ laborious procedures requiring skill and training or the use of sophisticated and expensive equipment, have a low efficiency of encapsulation or low encapsulation rate or involve encapsulating the drug simultaneously with the preparation of the vesicle, thereby invoking possible leakage of the encapsulated chemical. Also these methods leave a substantial portion of the substance sequestered outside of the vesicle since at best only 50% enclosed volumes of the encapsulated material relative to total volumes of the vesicles have been reported. These methods therefore require that expensive drugs used for encapsulation be recovered from the drug solution in which the vesicles were prepared. The prior art field of encapsulation methods thus has a number of very serious problems.

DISCLOSURE OF INVENTION

The present invention is directed to overcoming one or more of the problems as set forth above.

In accordance with an embodiment of the present invention, a method is set out for loading lipid-like vesicles having a membrane permeable to a chemical species to be loaded from a loading solution wherein the concentration of the loaded chemical species within the vesicle is greater than the concentration of the chemical species in the loading solution and the loaded chemical species can be substantially maintained within the vesicle for at least one-quarter hour following loading. The method comprises inducing a pH gradient across the vesicle membrane while the vesicle is in the loading solution containing the chemical species with the pH gradient having been selected to drive the chemical species into the vesicles.

In accordance with a second aspect of the present invention, a method is set out for loading lipid-like vesicles having a membrane permeable to a chemical species to be loaded and having the capability to maintain the loaded chemical species within the vesicle for at least one-quarter hour following loading by inducing a pH gradient across the membrane. The method comprises incorporating within the vesicle a buffer solution buffered to a selected acid or alkaline pH and having a selected molarity and at least one selected pka approximately equal to the selected buffer pH. The membrane is substantially impermeable to the buffer for at least one-quarter hour following loading of the chemical species and the vesicles are positioned in a bulk solution having a selected pH. The term "solution" is sometimes used loosely in the application to indicate a suspension in instances where lipid-like vesicles are present (i.e. suspended) in a solution.

The bulk solution is provided with a chemical species which has one or more selected acid pH responsive groups (i.e. groups which titrate as a function of pH by losing a negative charge upon being protonated) if the buffer is alkaline or one or more basic pH responsive groups (i.e. groups which titrate as a function of pH by becoming positively charged upon being protonated) if the buffer is acidic. The ph of the bulk solution is respectively at least 0.5, 0.3 or 0.2 of a pH unit higher than the pH of the buffer if the buffer is acidic and the chemical species has respectively one, two, or three or more basic pH responsive groups. The pH of the bulk solution is at least respectively 0.5, 0.3 or 0.2 of a pH unit lower than the pH of the buffer if the buffer is basic and the chemical species has respectively one, two, or three or more acid pH responsive groups.

The pH responsive groups of the chemical species having one or more acid pH responsive groups have a pKa that is generally lower than or equal to the pH of the bulk solution and generally higher than or equal to 3.5 and the pH responsive groups of the chemical species having one or more basic pH responsive groups have a pKa that is generally higher than or equal to the pH of the bulk solution and generally lower than or equal to 11.

In accordance with a third aspect of the present invention, a pharmaceutical preparation for administration in vivo to an animal is provided by the method of encapsulation described above. The chemical species in this instance is a drug. The osmolarity of the buffer within the vesicles is within the physiological range of the animal, the vesicles are suspended for administration in the bulk solution, and the pH of the bulk solution is physiologically benign.

In accordance with another aspect of the present invention, a kit is provided for loading lipid-like vesicles that have a membrane permeable to the chemical species to be loaded. The kit comprises a first compartment that has a first solution. The first solution has lipid-like vesicles incorporating a buffer buffered to a selected acid or basic pH. The buffer has at least one selected pKa approximately equal to the selected buffer pH and a selected molarity and cannot substantially permeate the vesicle for at least one-quarter hour following loading of the chemical species. The first solution also has a selected pH such that the stability of the vesicle and its buffer will be maintained for a period of at least one week at 4° C. The kit also comprises a second compartment, separate from the first compartment. The second compartment has a second solution that has a selected pH. Also included in the kit is a chemical species permeable to the vesicle. The chemical species has one or more selected acid pH responsive groups having selected pKas if the buffer is basic or one or more basic pH responsive groups having selected pKas if the buffer is acidic. The pH of the second solution is such that a mixture of the first and second solution will have a pH at least respectively 0.5, 0.3 or 0.2 of a pH unit higher than the pH of the buffer if the buffer is acidic and the chemical species has respectively one, two or three or more basic pH responsive groups or a pH at least respectively 0.5., 0.3 or 0.2 of a pH unit lower than the pH of the buffer if the buffer is basic and the chemical species has respectively one, two or three or more acid pH responsive groups. The pH responsive groups of the chemical species having one or more acid pH responsive groups have a pKa that is generally lower than or equal to the pH of a mixture of the first and second solutions and generally higher than or equal to 3.5. The pH responsive groups of the chemical species having one or more basic pH responsive groups have a pKa that is generally higher than or equal to the pH of a mixture of the first and second solutions and generally lower than or equal to 11. The chemical species is initially present in either one or the other of the two solutions.

In accordance with still another aspect of the present invention, another kit is provided for loading lipid-like vesicles having a membrane permeable to a chemical species to be loaded, the chemical species having acid or basic pH responsive groups. The kit comprises a first compartment that has a first solution having membranous lipid vesicles incorporating a buffer buffered to a selected alkaline pH if the chemical species to be loaded has acid pH responsive group or a selected acid pH if the chemical species has basic pH responsive groups. The buffer has at least one selected pKa approximately equal to the selected buffer pH, a selected molarity and cannot substantially permeate the vesicle membrane for at least one-quarter hour following loading of the chemical species. The first solution has a selected pH such that the stability of the vesicle and its buffer will be maintained for a period of at least one week at 4° C.

The kit further comprises a second separate compartment having a first substance (a compound or a second solution etc.) which when combined with the first solution will adjust the pH of the first solution so as to provide a predetermined pH gradient between the buffer within the vesicle and the pH adjusted first solution that will drive the chemical species into the vesicles. The kit also includes a third separate compartment having a second substance (yet another compound or a third solution etc.) which when combined with the pH adjusted first solution will further change the pH of said pH adjusted first solution to a value physiologically benign with regard to the blood of a mammal.

In accordance with still another aspect of the present invention, a method is provided for detoxifying an animal suffering from an overdose of a chemical species permeable to liposomes, the chemical species having basic or acid pH responsive groups (functions). The method comprises injecting the animal with a substantially physiologically benign solution having large volumes of liposomes having a buffer solution buffered to a pH generally lower than or equal to 5.4 if the chemical species' functions are basic pH responsive groups (amine, etc.) and a pH generally higher than or equal to 9.4 if the functions of the chemical species are acid pH responsive groups (carboxyl, etc.). The buffer also has a selected molarity within the physiological range of the animal and a selected pKa. The buffer also should not substantially permeate the vesicles for at least one hour after injection.

In accordance with a still further aspect of the present invention, a method is set forth for loading lipid-like vesicles having a membrane permeable to a chemical species to be loaded and for substantially maintaining the loaded chemical species within the vesicle for at least one-quarter hour following loading by inducing a pH gradient across the membrane. The method comprises incorporating within the vesicle a buffer solution buffered to a selected acid or alkaline pH and having a selected molarity at least one selected pKa approximately equal to the selected pH. The membrane is substantially impermeable to the buffer for at least one-quarter hour following loading. The vesicles are positioned in a bulk solution having a selected pH of either 0.5 to 3 pH units lower or higher than the pH of the buffer thereby establishing a transmembrane electrical potential. The inside of the vesicle will be positively charged if the pH outside of the vesicle is more acid than inside or the inside of the vesicle will be negatively charged if the pH outside the vesicle is more basic than inside. The bulk solution is provided with a chemical species having membrane-permeable negatively charged ions if the membrane charge within the vesicle is positive or membrane-permeable positively charged ions if the membrane charge within the vesicle is negative.

When operating in accordance with the various embodiments of the present invention, vesicles such as liposomes can be loaded with drugs or other chemicals by an untrained person who simply reads some accompanying instructions. Not only will the chemicals be encapsulated with a high degree of loading (since the concentration of the chemical in the vesicle is practically independent of the concentration of the chemical in the solution used to prepare the vesicles or the concentration of the chemical in the solution containing the vesicles), thereby allowing for maximum concentration of scarce and expensive chemicals, but the encapsulation can be done quickly and easily. Also, fear of degradation of the vesicles and leakage of the chemicals prior to administration need not be a concern, since the chemicals are easily encapsulated in the vesicles usually just before use, and the vesicles containing the chemical can be immediately delivered without further purification or other treatment provided the solution containing the loaded vesicles is physiologically benign. Drugs that have deleterious general effects such as chemotherapeutic or immunosuppressant drugs may be encapsulated in this manner and used to treat specific tissues or cells. Because of the high rate of encapsulation and the efficiency of encapsulation, concern over the expense and scarcity of the chemotherapeutic drugs no longer need be as great since only insignificant quantities of the drug will remain in the loading solution following vesicle preparation. Drugs encapsulated in this manner are sequestered within the vesicles (e.g., liposomes) until they reach the desired target tissue and are released when the membrane starts to break down and the drug begins to leak at the site of the desired tissue. (A process usually caused by lysosomal activity.)

DETAILED DESCRIPTION OF THE INVENTION

Figure 1:
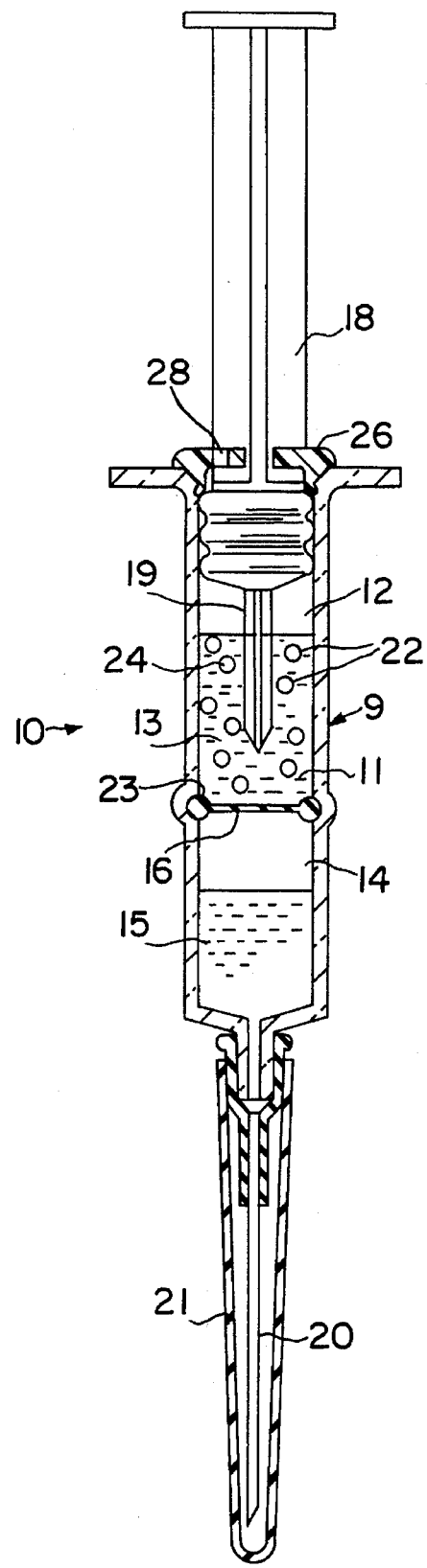
FIG. 1 illustrates an elevational view of an embodiment of the invention as contemplated herein.

In accordance with aspects of the present invention, a method and kits are provided for quickly and efficiently loading vesicles have a membrane permeable to a chemical species having one or more selected acid pH responsive groups or basic pH responsive groups by inducing a pH gradient across the membrane of the vesicle. The vesicles contain a buffer solution buffered to a selected acid pH if the pH responsive groups of the chemical species are basic or an basic pH if the pH responsive groups of the chemical species or drug are acid.

The movement of many molecules across a vesicle membrane involves proton gradients (pH gradients) as the driving force (Rottenberg, H., "The Measurement of Membrane Potential and Δ pH in Cells Organelles, and Vesicles", *Meth. Enzymol*, 55:547–569 (1979), Reinhold, L. and A. Kaplan, "Membrane Transport of Sugars and Amino Acids", *Ann. Rev. Plant Physiol.*, 35:45–83 (1984)). Electron spin residence (ESR) methods have been used to measure transmembrane pH gradients. Spin-labelled amines and carboxylic acids (amines and acids labelled with nitroxide free radicals) such as Tempamine and Tempacid have been used as probes to measure the pH gradient. These probes are freely permeable to the membranes and the relative concentration of the probes within the vesicles provided a direct measurement of the pH gradient. ESR spectroscopy monitors probe partitioning between the aqueous and membrane phases giving easily resolvable signals. The effectiveness of the spin labelled nitroxide probes for determining transmembrane pH gradients has been well documented in both bacterial and animal systems. (Mehlhorn, R. and I. Probst, *Meth. Enzymol.*, 88:334–344 (1982) and Melandri, B., R. Mehlhorn, and L. Packer, "Light-Induce Proton Gradients and Internal Volumes and Chromaphores of Rhodopseudomonas Spheaeroides", *Arch. Biochem. Biophys.*, 235:97–105 (1984). However, in these previous studies these pH responsive molecules (spin labelled amines and weak acids) were used only as probes. Since these studies involved the determination of transmembrane pH gradients only very low concentrations of the pH-responsive molecules could be used so as to avoid disturbing the pH gradient being studied which was generated as a result of natural processes, e.g., the so-called proton-motive force in mitochondrial respiration.

Before going into a more detailed explanation of the invention it will be useful to define some of the terms which are used herein. The term "lipid-like" is used broadly and includes oligolamellar lipid vesicles (liposomes), ufasomes and the like. The term "chemical species having one or more selected acid or basic pH responsive groups" is also used broadly to indicate any chemical or drug having acid or basic groups, properties or functions such as, but not limited to, amino or carboxyl groups. Other substances such as imidazoles and barbituric acid derivatives may also be used. The term also includes any chemical that has desired chemical or therapeutic properties that will not be sufficiently altered by the attachment of such pH responsive groups. The terms "hydrophobic positively and negatively charged ions" include delocalized (i.e. membrane-permeable) cations and anions that are designated as hydrophobic ions in the literature and are ions that are capable of transmembrane migration in their charged form. The terms "chemical species" and "drugs" include but are not limited to, such substances as chemicals, drugs for chemotherapy and immunosuppression, membrane permeable peptide toxins and hormones. Examples of drugs having molecules having basic properties are vincristine, doxorubicin, streptomycin, chloroquine and daunorubicin. Examples of drugs having molecules having acidic properties are derivatives of methotrexate, daunomycin, penicillin, p-amino salicylic acid and salicylic acid derivatives. Examples of drugs having hydrophobic ions are ellipticinium chloride, the antihelminthics, gentian violet and pyrvinium, pamoate and other cyanine dyes and the antimalarial drug pamaguine.

The preferred vehicle for delivering drugs or chemicals to an animal in vivo are liposomes but other lipid-like vesicles may also be used. General liposomal preparation has been fully disclosed in the literature (e.g. Miyamoto, V. K. and W. Stoeckenius, "Preparation and Characteristics of Lipid Vesicles," *J. Membrane Biol.*, 4:252–269 (1971) and U.S. Pat. No. 4,053,585). A simple highly effective preferred method for preparing vesicles is to stir soybean phosphatides (Asolectin, from Associated Concentrates) at room temperature for one-hour in either acidic or alkaline buffer and then to briefly sonicate this solution of lipids (approximately one minute). This procedure makes vesicles having large volumes of about 10 to 15 percent of the total aqueous volume within the vesicle.

The method and the kits utilize a preimposed pH gradient between the buffer in the vesicles and the solution containing the vesicles to cause the desired chemical or drug to be accumulated and encapsulated by the vesicles. The general rule is that for every unit of pH difference a tenfold accumulation of the chemical occurs. For drugs containing several titratable groups the accumulation behavior is altered. Thus a drug which has two amino groups, having pKa's that are greater than the pH of the final solution, can be accumulated a hundred-fold with a pH gradient of one unit. A drug with three such amino groups can be accumulated a thousand-fold in the presence of a one-unit pH gradient, etc. Conversely for a multi-acid drug, its pKa must be less than the pH of the final solution, for such substantial accumulation to occur.

The chemicals or drugs that may be incorporated using the present method of encapsulation include those species that have acid or basic pH responsive groups, hydrophobic delocalized charged ions or that may be provided with such. The vesicle is prepared by the entrapment of a buffer which will not permeate the membrane in the preparation of the vesicle. The buffer is selected so as to establish the pH gradient required to take up the specific chemical species or drug. The preparation of the vesicle is carried out by stirring and sonication. If the vesicles are to be administered, parenternally, in the solution that provides the external portion of the pH gradient, they are prepared in a buffer that is either more acidic or more alkaline than the physiological pH that they will encounter in the animal.

Subsequently the vesicles are treated with an alkaline or acid buffer, respectively, which will not permeate the vesicles membrane, thereby causing a pH change on the exterior but not interior of the vesicles. The resulting vesicles will therefore have a pH gradient between their interior and exterior. This gradient provides the driving force for accumulating the drug or chemical within the vesicle interior. As stated before, the larger the pH gradient, the larger the concentration gradient of the drug or chemical. Although a gradient of any magnitude will accumulate a drug, considerations of directing the drug to specific tissues, while minimizing its effects on non-targeted tissues dictate that the pH gradients be maximized.

The practical limits of the pH gradients are set by the tolerance of lipid-like material that is used in preparing the vesicles. For simple biological lipids like soybean phosphatides pH extremes of 4 and about 10.5 are readily tolerated for extended periods of time. The actual pH limits for a particular preparation of vesicles could be significantly larger, depending on how long the vesicles are to be stored which in turn depends on the stability of their lipid-like constituents. For example, vesicles to be loaded with amines are prepared in the presence of an acidic buffer such as citrate that has a pKa in the range of interest (usually about 5) and a pH of 4. This treatment ensures that the buffer will be contained within the liposome. Similarly, in cases where the liposomes are to be loaded with acidic molecules (carboxyl groups), the liposomes are prepared by sonication in the presence of a impermeable alkaline buffer that has a pKa of about 10.

Examples of appropriate acidic buffers other than citrate are tartrate or succinate. Appropriate alkaline buffer include besides carbonate lysine, lysine/phosphate and TAPS (obtainable from SIGMA). The buffer may not be permeable to the membrane therefore buffers such as TRIS may not be used. In addition the buffer should be chloride free since chloride promotes gradient decay (the effect of physiological chloride on decay is minimal).

After the vesicle has been prepared, the pH of the solution containing the vesicle is usually adjusted by the addition of an acid or a base to a pH of, respectively, at least about 0.5, 0.3 or 0.2 pH units higher than the pH of the buffer if the buffer is acidic and the chemical species has respectively one, two or three or more basic pH responsive groups and at least about 0.5, 0.3 or 0.2 pH units lower than the pH of the buffer if the buffer is basic and the chemical species has respectively one, two or three or more acid pH responsive groups. In instances where it is desirable to inject the animal immediately with the vesicle containing solution having the adjusted pH, the pH is adjusted to a physiologically benign value of between about 7 and about 7.8, preferably about 7.4. This adjustment of the pH by addition of an acid or base establishes a pH gradient that drives the weak acid or base (i.e., the chemical species), into the vesicle interior. The chemical's loading rate will depend on the pKa and will be complete within less than a minute for low molecular weight (MW less than 500) amine chemicals with pKas less than 10 and having no charge or strongly polar groups other than the amino group. Analogously, weak acids having pKas greater than 4 will accumulate in the liposomes in about one minute, unless they bear strongly polar groups other than their carboxyls. For simple amine chemicals having a pKa greater than 11 equilibration will be slower than one minute. Analogously, a simple weak acid having a pKa lower than 4 will require more than one minute for equilibration. For more polar compounds, equilibration rates have to be determined for the specific chemicals.

The membrane of the vesicle is impermeable to the passage of the buffer molecules throughout a pH range of 3 –11. The same membrane is permeable to a chemical species which has a pKa greater than about 4 pKa units, generally 5–7 pKa units, because of the significant chemical potential driving the species across the membrane.

Chemicals which do not contain amino groups or equivalent basic groups or carboxyl or equivalent acid groups are first converted to a derivative containing either an acid or a base moiety that will not seriously reduce the drug's therapeutic effect. In some instances it is desirable to prepare pro-drug moieties which will be converted into their desired active species by intracellular enzymes. Converting methotrexate to its monoester derivative as described in Example 4 is an example of such a pro-drug.

After incorporation the chemical will remain in the vesicle for fifteen minutes to several hours depending on the chemicals, until the buffer leaks out of the vesicle. One should be aware that decay of the initial drug content may occur because of dilution of the water volume outside of the vesicles when they are injected into an animal. This decay will generally occur much more slowly than the initial loading process because of favorable effects of the pH gradient on the vectorial movement of the drug across the vesicle membrane. This insures that a drug will reach its targeted tissue before significant leakage out of the vesicles can occur. This time period of usually several hours allows the chemical or drug to be carried to its desired destination and prevents it from acting in areas that would be deleterious to the animal.

This technique of incorporating a chemical species within a lipid-like vesicle containing a preselected buffer by means of a pH gradient can be used to rescue clinical patients who have received toxic overdoses of drugs having acid or basic pH responsive groups (amine or carboxyl functions, etc.). Such drugs include a host of molecules such as general anesthestics, barbiturates (weak acids), aspirin, and other salicylates (acids) for which antidotes are not available. Injections of large volumes of the liposomes suspended in a solution having a physiologically benign pH (usually about 7.4) can divert the drugs from their normal biological targets such as nerve cells to the liver where they will be metabolized and henced detoxified. For some drugs like aspirin, where elimation from the body does not involve significant liver metabolism, liposome injection would nevertheless provide a means for diminishing the toxic effect of the drug by reducing high blood concentrations during the initial phase of intoxication. The liposomes containing the toxin may also be removed by means of dialysis.

The kits, as described above, also utilizes a pH gradient to load lipid-like vesicles. Referring now to FIG. 1, it will be noted that the kit apparatus illustrated comprises a syringe (10) having a glass, plastic, etc. barrel (9) having a first compartment (12), having a first solution (13) and a second compartment (14) having a second solution (15). The first compartment (12) is separated from the second compartment (14) by an impermeable barrier (16) made of rubber, plastic or the like. The syringe (10) also comprises a plunger (18) and a needle (20). The needle is surrounded by a protective sheath (21). The first solution (13) contains the membranous vesicles (22) magnified in size in FIG. 1 so as to be visible, containing a buffer (24) having either an acid or alkaline pH. In most instances the buffer (24) and the first solution (13) will be identical with the vesicles (22) having been prepared in the first solution (13).

The syringe (10) also contains the chemical (11) to be loaded. The chemical (11) is present in the solution which affords it the greatest stability and may therefore be in either the first or second solution (13, 15) depending upon the properties of the chemical and the solutions. For purposes of illustration, the chemical (11) in FIG. 1 is located in the first solution (13). The second solution (15) is an acid if the buffer (24) inside the vesicles (22) is a base and a base if the buffer (24) inside the vesicles (22) is acidic. The second solution (15) has a pH such that a mixture of said first and second solutions (13, 15) will have a pH, respectively, of at least about 0.5, 0.3 or 0.2 pH units higher than the buffer (24) if the buffer (24) is acidic and the chemical (11) has respectively one, two or three or more basic pH responsive groups and at least about 0.5, 0.3, or 0.2 pH units lower than the pH of the buffer (24) if the buffer (24) is basic and the chemical (11) has respectively, one, two or three or more acid pH responsive groups. To encapsulate the chemical (11) within the vesicles (22), the syringe (10) is turned with the needle (20) facing upwards (the opposite direction from FIG. 1) and the plunger (18) is forced upward just enough to create enough pressure to break the barrier (16). The barrier may also be broken by a sharp implement (19) attached to the plunger (18). In this instance the implement (19) is prevented from damaging the barrel (9) by a stop (23). The volume of the second solution (15) in the second compartment (14) should be such that when the barrier (16) is broken only a minimal amount of solution will enter the needle (20). Once the barrier (16) is broken the plunger (18) is withdrawn to around its initial position at the top of the first compartment (12). The syringe (10) is then agitated and the two solutions are allowed to mix for an appropriate period of time. If the resulting pH of the mixture of the first and second solutions (13, 15) is physiologically benign the entire mixture including the vesicles (22) containing the now encapsulated chemical species may be injected directly into an animal. For facilitation in operating the plunger (18) the syringe may have a block (26) at the bottom of the barrel (9) with an air hole (28).

Figure 2:
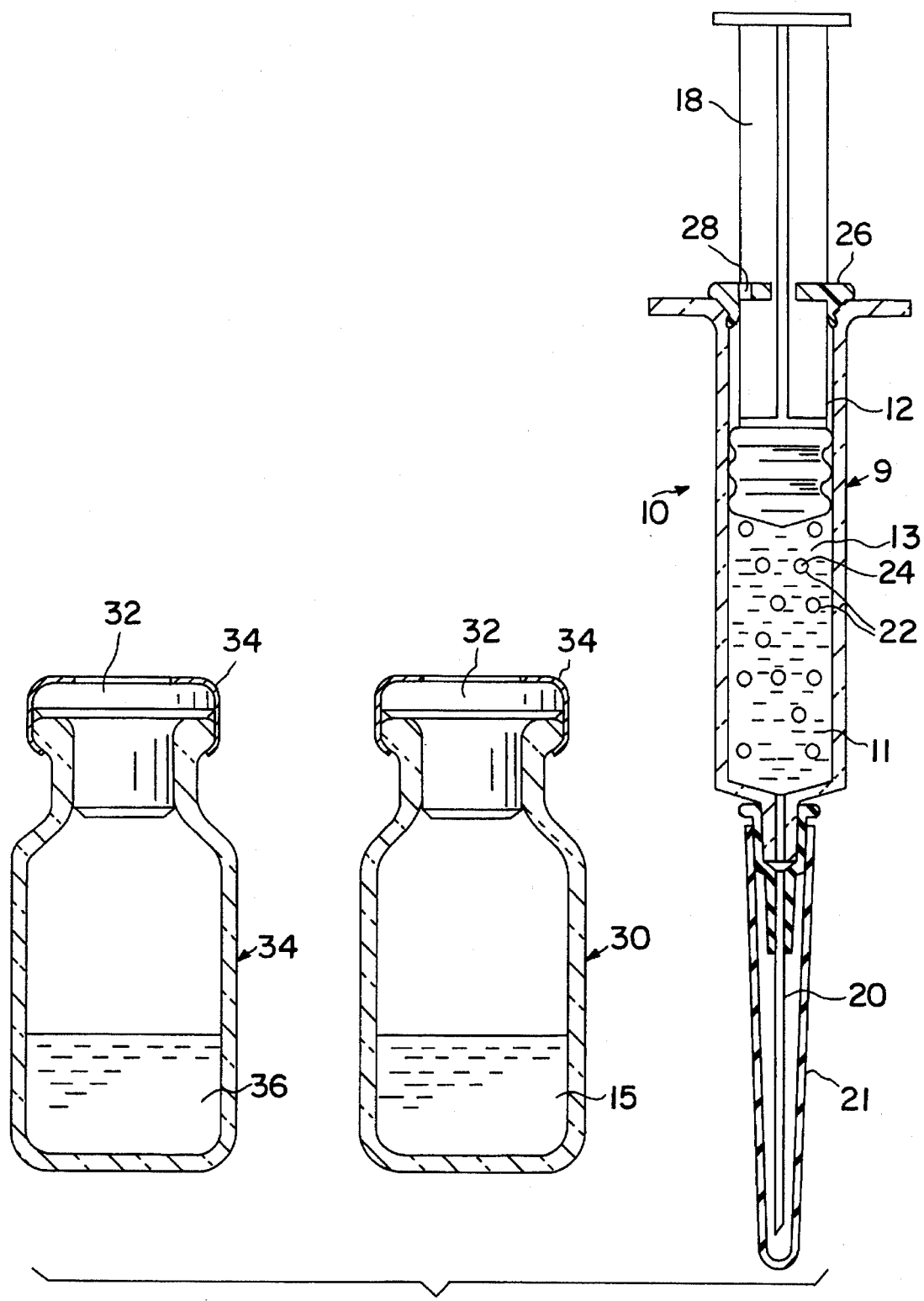
FIG. 2 illustrates an elevational view of another embodiment of the invention.

FIG. 2 illustrates another embodiment of the invention. This embodiment is better understood by way of reference to FIG. I of the drawings whereas like numbers in FIGS. 1 and 2 refer to like parts. In this instance, the barrel (9) has only one compartment (12) containing a solution (13) having vesicles (22) containing the buffer (24). To encapsulate the chemical (11) which may or may not be included with the kit but which for purposes this illustration is included in the first solution (13), the contents of the syringe (10) are emptied into a first vial (30). The first vial (30) may be composed of glass, plastic or the like. The contents of the barrel (9) are emptied into the first vial (30) by piercing the rubber septum (32) with the needle (20) and pushing the plunger (18) downward. The rubber septum (32) is kept in place by a retaining clip (34). The first vial (30) also contains a second solution (15) which is an acid if the buffer (24) is a base and a base if the buffer (24) is acidic. The second solution (15) has a pH such that mixture of said first and second solutions (13, 15) will have a pH respectively of at least about 0.5, 0.3 or 0.2 pH units higher than the buffer (24) if the buffer (24) is acidic and the chemical (11) has respectively one, two, or three or more basic pH responsive groups and at least about 0.5, 0.3 or 0.2 pH units lower than the pH of the buffer (24) if the buffer (24) is basic and the chemical species has respectively, one, two, or three or more acid pH responsive groups. The first solution (13) and the second solution (15) are allowed to mix to encapsulate the chemical (11) and the syringe (10) is refilled and emptied several times. The procedure described above is repeated for a second vial (35). The second vial contains a third solution (36) which is acid if the combination of the first and second solution (13, 15) is basic and basic if the combination is acid. In addition the pH of the third solution (36) has been calculated so as to render the mixture of all three solutions physiologically benign with regard to the blood of a mammal.

EXAMPLE 1

Liposomes of soybean lipids were prepared according to a variation of Miyamoto and Stoeckenius, supra by sonication of 1 gm of asolectin in the presence of 10 mls of 100 mM sodium citrate at pH 5.0. Spin-labeled primary amine Tempamine (Aldrich Chemical Co.) was added to 50 µM citrate solution containing the pre-sonicated vesicles to give a final concentration of 20 µM, and a sufficient amount of 5 molar sodium hydroxide was also added to the solution to raise the pH of the solution to 7.4. This resulted in a 300-fold accumulation of the Tempamine inside the vesicles within one minute of the addition of the base. The rate of uptake of the amine depends on the pKa of the amine. As determined by ESR spectroscopy the resulting pH gradient was stable for several hours.

EXAMPLE 2

Liposomes were prepared by sonicating 0.5 grams of asolectin in 10 mls of 100 mM sodium citrate buffer, pH 4. An amount of 542 microliters of five normal sodium hydroxide was added. This raised the pH of the bulk solution containing the liposomes to 7.4. An intravenous catheter system consisting of a 27-gauge needle, connected to a 1.0 ml syringe by 4 inches of PE20 (polyethylene) plastic tubing was used for the infusion of the liposome suspension into the lateral tail veins of two female Wistar rats, 250 grams each. The liposome suspension was infused into the rats at a rate of about 0.2 mls per minute until a total volume of 0.7 mls had been infused. The rats appeared somewhat disoriented upon completion of the infusion, and release from the restraining cones, but otherwise none the worse from the experience. One hour later the animals were examined and were completely normal in appearance, and after one week's observation, no long-term effects of the infusion could be detected.

EXAMPLE 3

Lipid vesicles, containing 15 mg/ml of Sigma Type II-S phosphatidyl choline were prepared by sonication in a 120 mM lysine/phosphate buffer (chloride-free) at pH 10.5. The total sonication time was three minutes, with intermittent cooling. The vesicles were incubated for two minutes with 20 µM of a spin-labeled carboxylic acid, prepared by reacting 1M succinic anhydride with one equivalent of Tempamine in chloroform, in the presence of a sufficient amount of a 100 mM citric acid to lower the external pH to 6 (approximately 1 volume equivalent). Analysis of the intravesicular concentration of the spin-labeled acid by ESR spectroscopy revealed that a more than 1,000-fold increase had occurred in response to the imposed pH gradient.

The vesicles were then transferred into a piece of dialysis tubing that had been spread into a flattened geometry to minimize the diffusion path of internal molecules to its surface. When the dialysis tubing was placed in a large volume of phosphate buffer in isotonic saline solution, this system simulated the physiological situation that would arise when vesicles are injected into the blood, where dilution of the drug outside the vesicles would occur as the vesicles moved through the circulation. When the tubing was placed into a beaker containing more than a ten-fold excess of lysine buffer; the pH gradient that had been preimposed was largely collapsed upon mixing of the aqueous phases inside and outside of the tubing. Table I shows the kinetics of efflux of the spin-labeled acid out of the dialysis tubing, and also shows the kinetics of the same probe when incubated with vesicles that have not been subjected to a pH gradient.

It is clear from the data in Table I that when the intradialysis concentration of probes was examined at the end of the incubation period, the vesicles that had been loaded with the pH gradient had retained a much higher concentration of the acid than those without a pH gradient. This example also indicates that it is unnecessary to maintain the pH gradient subsequent to the chemical loading procedure.

TABLE I

ESR signal leaking out of dialysis tubing containing vesicles that had been incubated with a spin labelled carboxylic acid in the presence and absence of a pH gradient

| No pH gradient | | pH gradient | |
| --- | --- | --- | --- |
| Time (min) | ESR signal | Time (min) | ESR signal |
| 3 | 0.09 | 15 | 0.11 |
| 10 | 0.15 | 30 | 0.12 |
| 20 | 0.17 | 45 | 0.15 |
| 40 | 0.18 | | |
| internal | 0.24 | internal | 3.0 |

EXAMPLE 4

Methotrexate is converted to its monoester deriverative by synthesizing methotrexate from the monomethyl ester of glutamate rather than from glutamate itself by conventional methods for methotrexate synthesis. Liposomes are prepared as in Example 3 and the vesicles are incubated for about ten minutes with 1 mg ml of the methotrexate derivative in the presence of a sufficient amount of 100 mM citric acid to lower the external pH to 4 (approximately one volume equivalent). The methotrexate is thereby internalized within the vesicles. The external pH is adjusted to 7.4 and 0.1 ml of the solution is injected into mice representing approximately 4% of total fluid body volume (2.5 ml).

EXAMPLE 5

Liposomes are prepared according to Example 1 or 2 and are concentrated by means of a standard filtration concentration to a concentration of approximately 50 mg asolectin per 1 ml of 100 mM sodium citrate. The resulting lipid-like solution is injected in mice as described in Example 2 such that the final infusion is approximately 1% of total fluid body volume of asolectin. This example indicates that large volumes of liposomes having substantial pH gradients can be injected into animals without serious adverse effects.

EXAMPLE 6

Loading of hydrophobic ions

Vesicles are prepared at pH 4.5 as before. The vesicle solution contains 10 μM of the cyanine dye dithiazanine iodide. To achieve internalization of the cyanine dye, the vesicles are mixed with a 100 mM solution of sodium triphosphate of sufficient volume to raise the pH of the mixture to 7.4. This generates a pH gradient acid-inside in the vesicles and this pH gradient in turn generates an electrical gradient of about 180 millivolts, negative inside the vesicles. The positively charged cyanine dye, whose delocalized charge renders it membrane permeable, is driven into the vesicle interior in response to the electrical potential, reaching a final accumulation of a thousand fold relative to the aqueous solution outside of the vesicles. Since the vesicles are prepared with a internal volume of about 10%, the final cyanine concentration inside the vesicles is about 100 μM, while the external cyanine concentration is about 100 nM.

INDUSTRIAL APPLICABILITY

In accordance with the present invention, kits and methods are provided for encapsulating any number of drugs within lipid-like vesicles. A method for detoxifying an animal is also described. The kits are very easy to use and require little or no training for the operator. They are fast and provide a high rate of encapsulation. Although the foregoing invention has been described in some detail by way of illustration and example for the purposes of clarity and understanding, it should be recognized that changes and modifications may be practiced within the scope of the appended claims.

I claim:

1. A method of detoxifying an animal suffering from an overdose of a chemical species with basic pH responsive groups comprising injecting the animal with a solution having a physiologically benign pH with respect to the animal, the solution having large volumes of liquid crystalline liposomes having a buffer solution buffered to a pH generally lower than or equal to 5.4 and the buffer having at least one selected pKa and a selected molarity within the physiological range of the animal, the liposomes being substantially impermeable to the buffer for at least one hour after injection.

2. A method for detoxifying an animal suffering from an overdose of a chemical species with acid pH responsive groups the chemical species being permeable to liposomes comprising: injecting the animal with a solution having a physiologically benign pH with respect to the animal, the solution having large volumes of liquid crystalline liposomes having a buffer solution buffered to a pH generally higher than or equal to 9.4 and having a selected molarity and selected pKa, the liposomes being substantially impermeable to the buffer for at least one hour after injection.

* * * * *